US00PP21351P2

(12) United States Plant Patent
Fafard

(10) Patent No.: US PP21,351 P2
(45) Date of Patent: Sep. 28, 2010

(54) ***LIGULARIA* PLANT NAMED 'OSIRIS CAFE NOIR'**

(50) Latin Name: *Ligularia dentata*
Varietal Denomination: Osiris Café Noir

(76) Inventor: Serge Fafard, 818 rue Monique. St-Thomas de Joliette, Quebec (CA) J0K 3L0

( * ) Notice: Subject to any disclaimer, the term of this patent is extended or adjusted under 35 U.S.C. 154(b) by 0 days.

(21) Appl. No.: 12/586,012

(22) Filed: Sep. 16, 2009

(51) Int. Cl.
*A01H 5/00* (2006.01)

(52) U.S. Cl. ..... Plt./448
(58) Field of Classification Search ..... Plt./448
See application file for complete search history.

*Primary Examiner*—Annette H Para
(74) *Attorney, Agent, or Firm*—Penny J. Aguirre

(57) ABSTRACT

A new cultivar of *Ligularia dentata*, 'Osiris Café Noir', characterized by its ovate-shaped leaves with margins that are incised and undulating with conspicuous veining, its foliage that emerges deep purple-black in color and transitions through shades of bronze before maturing to olive green, its lower leaf surfaces that are red-purple in color, its short plant height, its yellow-orange flowers that are present in late summer to early fall and its cold hardiness in U.S.D.A Zone 3.

2 Drawing Sheets

Botanical classification: *Ligularia dentata.*
Cultivar designation: 'Osiris Café Noir'.

BACKGROUND OF THE INVENTION

The present invention relates to a new and distinct cultivar of *Ligularia dentata* and is hereinafter referred to by the cultivar name 'Osiris Café Noir'.

The new cultivar resulted from an ongoing breeding project that commenced in 1994 in St-Thomas de Joliette, Quebec, Canada when the breeder discovered a unique seedling that arose from seed of *Ligularia* 'Othello' (not patented) in 1994. Multiple crosses and re-crosses were made with this seedling and its progeny with the goal of creating new cultivars of *Ligularia* with unique plant forms and leaf colors. 'Osiris Café Noir' derived from a cross made by the Inventor in 2000 between separate plants of *Ligularia* 'Osiris Fantaisie' (U.S. Plant Pat. No. 19,302) as the male and female parents. The new cultivar was selected as a single unique plant from the resulting seedlings of the cross in 2005.

Asexual reproduction of the new cultivar was first accomplished under direction of the Inventor by in vitro propagation in Rijswijk, The Netherlands in December of 2006. Asexual reproduction of the new cultivar by division and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Osiris Café Noir' as a new and unique cultivar of *Ligularia.*

1. 'Osiris Café Noir' exhibits leaves that are ovate in shape with distinct veining and margins that are deeply incised and undulating.
2. 'Osiris Café Noir' exhibits foliage with a unique coloration that emerges deep purple-black and then transition through shades of bronze before maturing to olive green.

3. 'Osiris Café Noir' has a lower leaf surface that is flushed with red-purple.
4. 'Osiris Café Noir' is short is stature with the foliage reaching a height of 76 cm (1 m in bloom) in Quebec, Canada.
5. 'Osiris Café Noir' has yellow-orange flowers in corymbs that arise above the foliage in late summer into fall on purple stems (similar to its parent plant).
6. 'Osiris Café Noir' is cold hardy in U.S.D.A. Zone 3.

'Osiris Café Noir' can be mostly closely compared to its parent plant 'Osiris Fantaisie'. 'Osiris Fantaisie' is similar to 'Osiris Café Noir' in having leaves that are ovate in shape with distinct veining and margins that are deeply incised and undulating, and in having lower leaf surfaces that are flushed with red-purple, however 'Osiris Fantaisie' differs from 'Osiris Café Noir' in having leaves that are deep green in color and flushed with purple as they mature. 'Osiris Café Noir' can also be compared to 'Othello', a descendant in the breeding line of 'Osiris Café Noir'. 'Othello' differs in having more kidney-shaped leaves with margins that are finely serrated and lack undulations, in exhibiting smaller flowers, and in being taller in height. 'Osiris Café Noir' can also be compared to *Ligularia dentata* cultivars 'Desdemona' and 'Brit-Marie Crawford' (both unpatented). Both of these cultivars are similar to 'Osiris Fantaisie' in being short in stature and in having leaves that are flushed purple on the lower surface, however the leaves of 'Desdemona' and 'Brit-Marie Crawford' are kidney-shaped with margins that are less serrated and less undulated, and the upper surfaces of the leaves are brown-purple in color.

BRIEF DESCRIPTION OF THE DRAWING

The accompanying colored photographs illustrate the overall appearance and distinct characteristics of the new *Ligularia*. The photographs in the figures were taken of a plant and plant parts of a one year-old plant of 'Osiris Café Noir' as grown outdoors in a 4-liter container in The Netherlands.

DETAILED BOTANICAL DESCRIPTION OF THE PLANT

Figure 1:
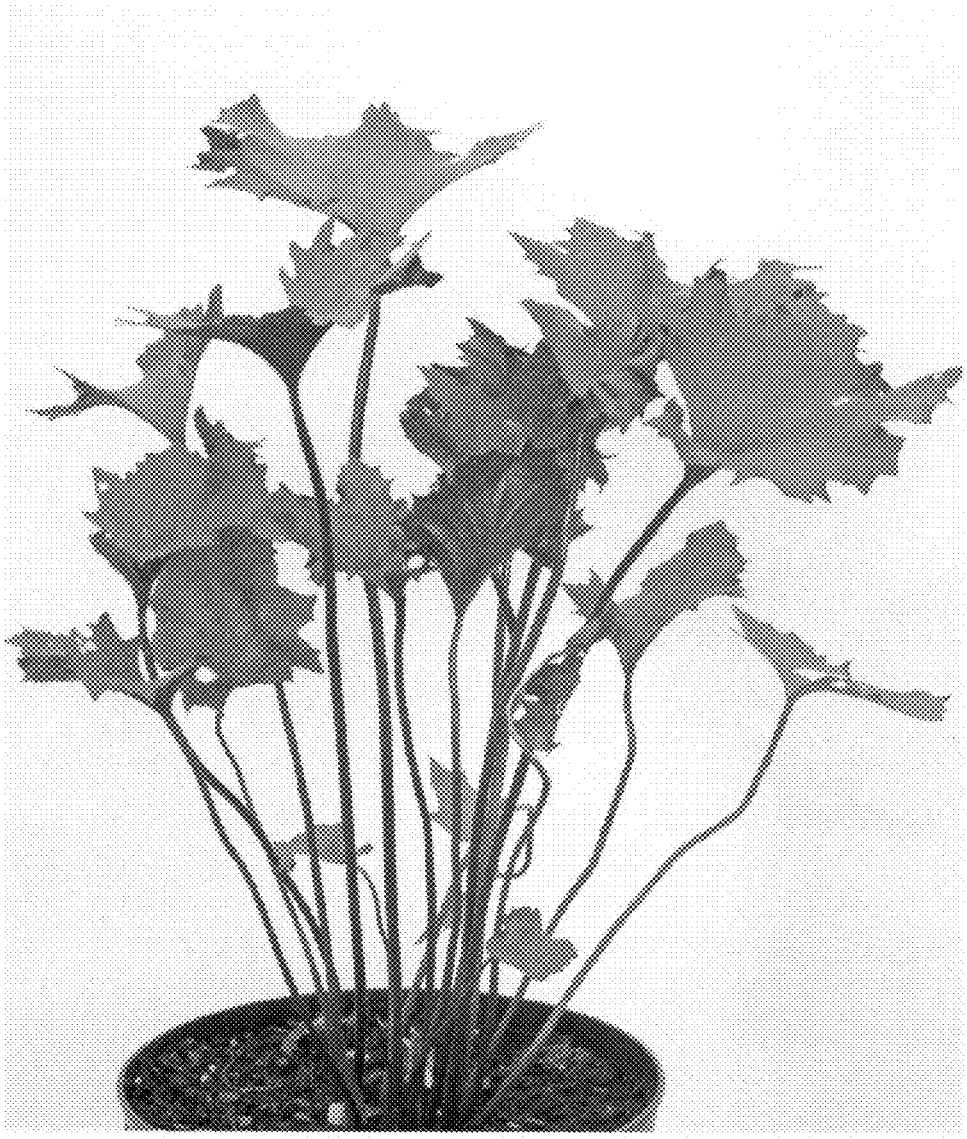
FIG. 1 provides a view of the habit and foliage characteristics of the new cultivar.
Figure 2:
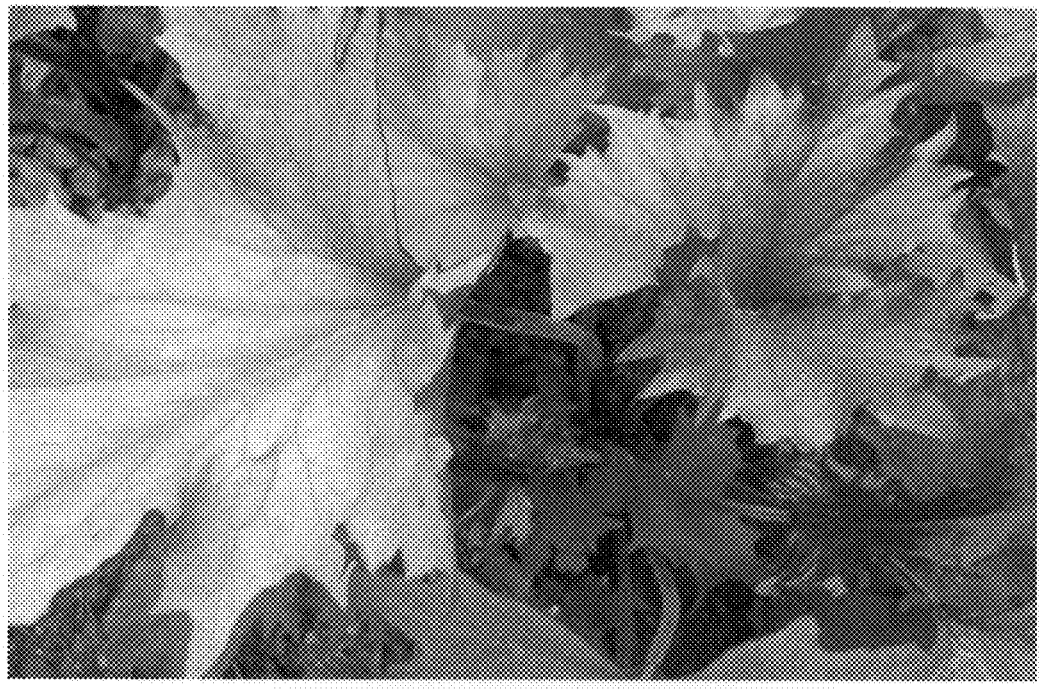
FIG. 2 shows a close-up view of change in foliage coloration during maturation and FIG. 3 provides a close-up view of a flower. The colors in the photographs may differ slightly from the color values cited in the detailed botanical description, which accurately describe the colors of the new *Ligularia*.
Figure 3:
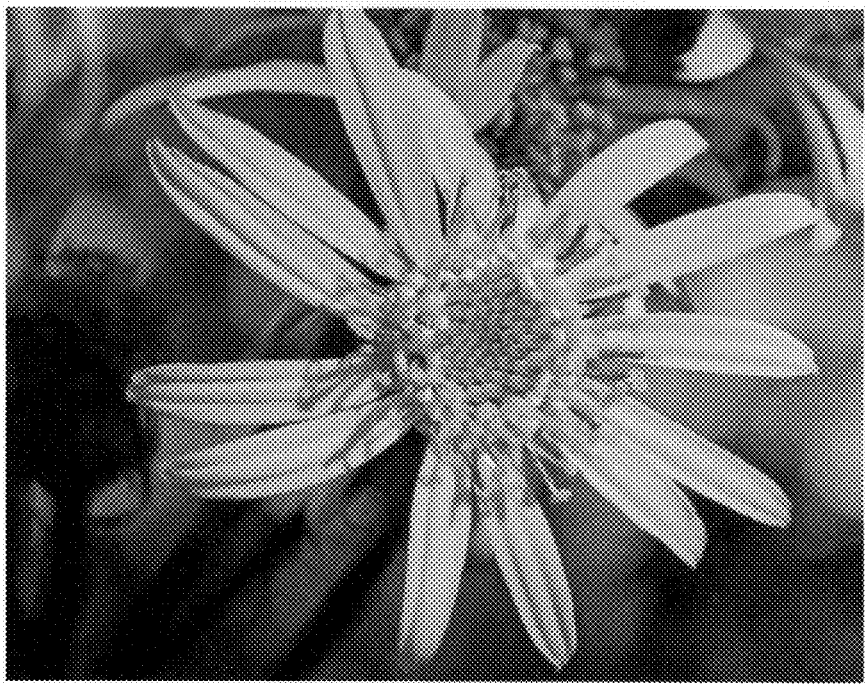

The following is a detailed description of one year-old plants of 'Osiris Café Noir' as grown in 4-liter containers in The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit.*—Blooms from August to early October in Quebec, Canada.

*Plant habit.*—Clump-forming, robust, herbaceous perennial, vase-shaped.

*Height and spread.*—Reaches about a height of about 76 cm (1 m in height in bloom) and about 91 cm in width.

*Cold dardiness.*—U.S.D.A. Zone 3.

*Diseases and Pests.*—Disease and pest free under the conditions tested.

*Root description.*—Fibrous.

*Branching habit.*—Basal foliage on long petioles.

*Propagation.*—In vitro propagation is the preferred method, division are also possible.

*Growth rate.*—Moderate.

Foliage description:

*Leaf shape.*—Broadly ovate.

*Leaf division.*—Simple.

*Leaf base.*—Cuneate.

*Leaf apex.*—Acute.

*Leaf venation.*—Primary palmate, secondary net-veined, uniquely conspicuous, color on upper surface 187A, color on lower surface N186C and 187A.

*Leaf margins.*—Incised, often tripartite (oak-like), undulating, incised lobes dentate.

*Leaf attachment.*—Petiolate.

*Leaf arrangement.*—Radicalis.

*Leaf orientation.*—Held about 45° to petiole.

*Leaf surface.*—Sparsely pubescent and semi-glossy on upper surface and glossy on lower surface with pubescence on veins.

*Leaf color.*—Emerging leaves upper and lower surface; N77A, maturing leaves upper surface; a color between 146A and 147A flushed with N77A, mature leaves upper surface; gradually turning to a blend of 151A and 146A, maturing leaves lower surface; N186A, mature leaves lower surface; a color between N186C and 187A.

*Leaf size.*—Matures to an average of 11 cm in length and 13.2 cm in width.

*Leaf quantity.*—New leaves continuously produced, an average of 19 by mid summer on a one year-old plant.

*Petioles.*—Oval in shape, orientation ranges from vertical to a 45° angle, average of 29.2 cm in length and 4 mm in width, matures to 187A in color, surface is glabrous but sparsely covered with white hairs near leaf blade attachment.

Flower description:

*Type.*—*Capitulum*, heterogamous with ray florets around the head margin and disk florets in the center, forming a radiant head, arranged in corymbs.

*Capitulum number.*—3 to 5 per peduncle branch, about 25 per flowering stem.

*Lastingness of inflorescence.*—3 to 4 weeks until senescence of ray florets, disk flowers are persistent, a cut flower will last about 10 days.

*Capitulum size.*—Matures to about 2 cm in depth and 7 cm in diameter, disk size is about 1.5 cm diameter.

*Fragrance.*—Slight rose scent.

*Phyllaries.*—About 16 arranged in a single row to form a campanulate involucre, about 1 cm in length and 2 mm in width, fused at base, acute apex, broadly lanceolate in shape, 138A to flushed with 178B in color, entire margin and glabrous on upper surface and hairy on inner surface.

*Buds.*—Cup-shaped, average of 1.5 cm in diameter and depth, phyllary are 138A to flushed with 178A and disk florets appear 178C in color when viewed in mass just prior to opening and short upright rays florets 15B with flushed of 34C.

*Peduncle.*—Branched, main peduncle about 55 cm in length and an average of 4 mm in width with 3 to 5 branches with an average of 12 cm in length and about 2.5 mm in width, 178A in color, texture is dull and sparsely covered with white hairs, one to two leaves, same coloration as basal leaves with petioles about 7 mm in length and 4 mm in width with leafy base and 187A and 187B in color.

*Pedicels.*—Range from 187A to 187B in color, an average of 5.2 cm in length and 2 mm in width, surface is dull and sparsely covered with fine white hairs.

*Ray florets* (*female*).—Average of 12, oblanceolate to narrowly elliptic in shape, vertical ridges on both surfaces, about 2.6 cm in length and 7 mm in width, emarginated apex, cuneate base, entire margin except apex, glabrous in texture, initially held upright about 70° from horizontal and become horizontal to reflexed as they mature, color of upper and lower surface when opening; 17A flushed with 34C, color of upper and lower surface when mature; 15A, pappus about 5 mm in length at apex of ovary.

*Disk flowers* (*bisexual*).—About 40, tubular in shape, arranged spirally on a conical receptacle, about 1.5 in length and 2 mm in width, pappus comprised of about 30 bristles about 7 mm in length and 178B in color; color emerges 17A flushed with 178C at apex, mature florets color is defined by the reproductive organs extending beyond the apex of the floret, base of floret changing to a blend of N199C and 178A.

Reproductive organs:

*Gynoecium.*—Pistil; 1, about 1.1 cm in length and 1.5 mm in width, style; 0.3 mm in width and 9 mm in length, 5D in color, surrounded by stamens, stigma; bifid, each arm is reflexed and about 2 mm in length and 14A in color, ovary; inferior, about 4 mm in length, 1 mm in width, and 145C in color.

*Androecium.*—Stamens; 4, un-fused, coherent in cylinder around style, anthers; 4 mm in length and 0.3 mm in width, basifixed, dehisced longitudinally, 200A in color filaments; 5 mm in length, 0.3 mm in width, 145C in color, pollen; abundant and 22A in color.

*Fruit.*—A terete with pappus, 199A in color.

It is claimed:

1. A new and distinct of *Ligularia* plant named 'Osiris Café Noir' as herein illustrated and described.

* * * * *